United States Patent
Zaleske et al.

(10) Patent No.: US 6,183,737 B1
(45) Date of Patent: Feb. 6, 2001

(54) BONDING OF CARTILAGE PIECES USING ISOLATED CHONDROCYTES AND A BIOLOGICAL GEL

(75) Inventors: David J. Zaleske, Weston, MA (US); Giuseppe Peretti, Milan (IT); Enzo Caruso, Allston, MA (US); Francesco Rossetti, Milan (IT); Mark Randolph, Chelmsford, MA (US)

(73) Assignee: The General Hospital Corporation, Boston, MA (US)

(*) Notice: Under 35 U.S.C. 154(b), the term of this patent shall be extended for 0 days.

(21) Appl. No.: 09/182,379

(22) Filed: Oct. 29, 1998

Related U.S. Application Data

(60) Provisional application No. 60/064,451, filed on Oct. 30, 1997.

(51) Int. Cl.⁷ .............................. A61F 2/00; A01N 1/00; C12N 5/00; C12N 11/04; C12N 11/02
(52) U.S. Cl. ..................... 424/93.7; 424/423; 424/426; 435/1.1; 435/177; 435/178; 435/180; 435/182; 435/325; 435/395; 435/397; 623/11
(58) Field of Search .................................. 435/395, 397, 435/325, 174, 177, 178, 180, 182; 424/422, 423, 93.7, 426; 623/16, 11; 128/898

(56) References Cited

U.S. PATENT DOCUMENTS

| | | | |
|---|---|---|---|
| 4,642,120 | 2/1987 | Nevo et al. ............................ | 623/16 |
| 5,549,904 | 8/1996 | Juergensen et al. ................. | 424/423 |
| 5,631,011 | 5/1997 | Wadstrom ............................ | 424/400 |
| 5,658,343 | 8/1997 | Hauselmann et al. ................. | 623/20 |
| 5,736,132 | 4/1998 | Juergensen et al. ................. | 424/94.5 |
| 5,759,190 | 6/1998 | Vibe-Hansen et al. ............. | 606/151 |
| 5,842,477 | 12/1998 | Naughton et al. .................... | 128/898 |

FOREIGN PATENT DOCUMENTS 0 339 607   2/1989   (EP).

OTHER PUBLICATIONS

Jurgensen et al., "A New Biological Glue for Cartilage–Cartilage Interfaces: Tissue Transglutaminase", The Journal of Bone and Joint Surgery, Inc. 79–A:185–193, 1997.

Pitman et al., "The Use of Adhesives in Chondrocyte Transplantation Surgery: In–Vivo Studies", Bull. Hosp. JT Dis. Orthop. Inst. 49:213–220, 1989.

Quatela et al., "Effects of Cyanoacrylate Tissue Adhesives on Cartilage Graft Viability", Laryngoscope 103:798–803, 1993.

Hendrickson et al., "Chondrocyte–Fibrin Matrix Transplant for Resurfacing Extensive Articular Cartilage Defects", Journal of Orthopaedic Research 12:485–497, 1994.

Homminga et al., "Chondrocyte Behavior in Fibrin Glue In Vitro", Acta Orthop Scand 64(4):441–445, 1993.

Hunziker et al., "Biological Basis for Repair of Superficial Articular Cartilage Lesions", 38th Annual Meeting, Orthopaedic Research Society, Feb. 17–20, 1992, Washington, D.C. p. 231.

Reindel et al., "Integrative Repair of Articular Cartilage In Vitro: Adhesive Strength of the Interface Region", Journal of Orthopaedic Research 13:751–760, 1995.

Wirth et al., "Techniques of Cartilage Growth Enhancement: A Review of the Literature", Arthroscopy: The Journal of Arthroscopic and Related Surgery 12(3):300–308, 1996.

*Primary Examiner*—David M. Naff
(74) *Attorney, Agent, or Firm*—Fish & Richardson P.C.

(57) ABSTRACT

Isolated chondrocytes are propagated in the presence of a biological gel such as a fibrin gel to generate a cartilage matrix that firmly bonds together two adjacent cartilage pieces. A bonding composition containing the isolated chondrocytes mixed with the biological gel is applied to a surface of one (or both) of the cartilage pieces, and the surface is contacted with the other cartilage piece. In a different order of steps, the two cartilage pieces are held in apposition, and gaps at the interface are filled with the bonding composition. In another method, either or both of the cartilage pieces are first incubated with the isolated chondrocytes, the biological gel is then applied, and the cartilage pieces are held together. Alternatively, after incubating with isolated chondrocytes, the biological gel can be applied to fill gaps at the interface between cartilage pieces held in apposition. One or both of the cartilage pieces can be depleted of endogenous chondrocytes before bonding, and the cartilage pieces can be articular cartilage, fibrocartilage or growth cartilage. A cartilage implant is formed by incubating isolated chondrocytes with a cartilage piece and applying the biological gel to the incubated cartilage piece. In repairing defective articular cartilage in a mammal, one of the pieces to be bonded is the defective cartilage and the other piece is the cartilage implant. A meniscal tear in fibrocartilage is another cartilage defect that can be repaired.

4 Claims, 2 Drawing Sheets

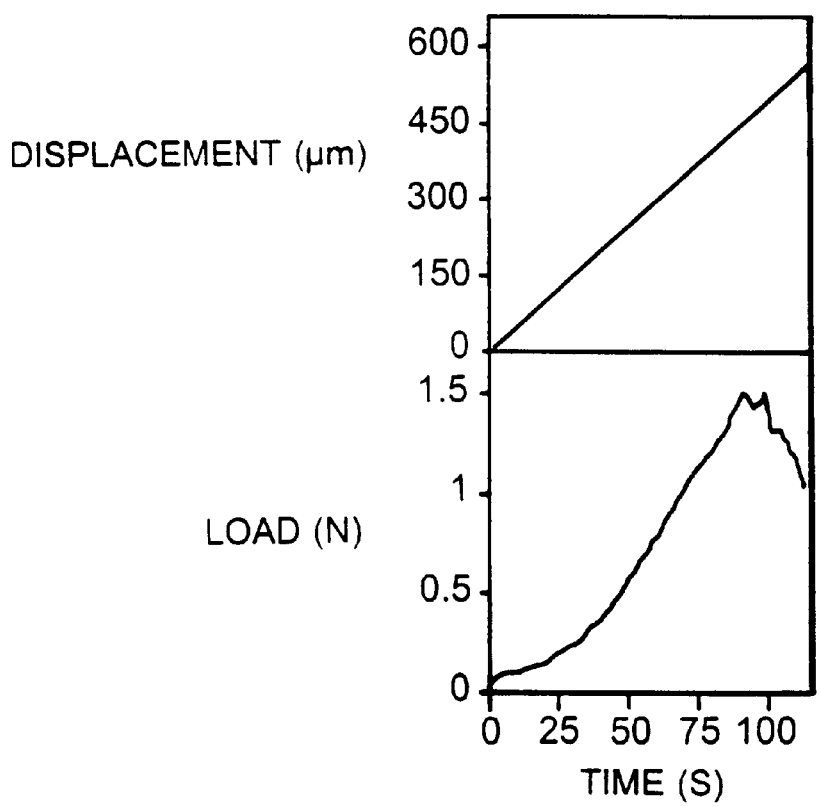
FIG. 1A
FIG. 1B
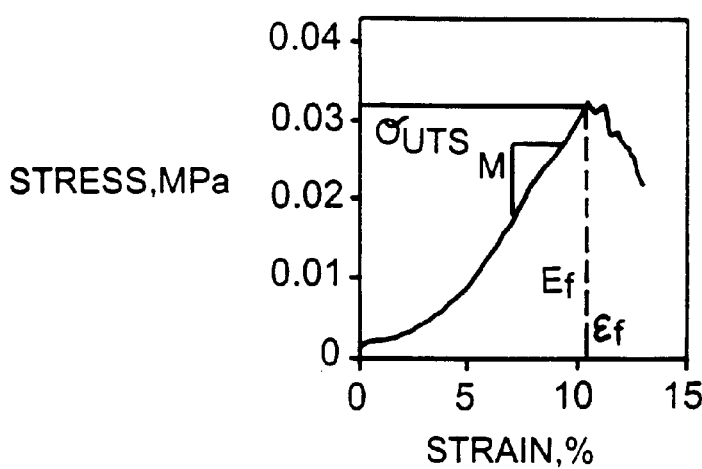
FIG. 1C

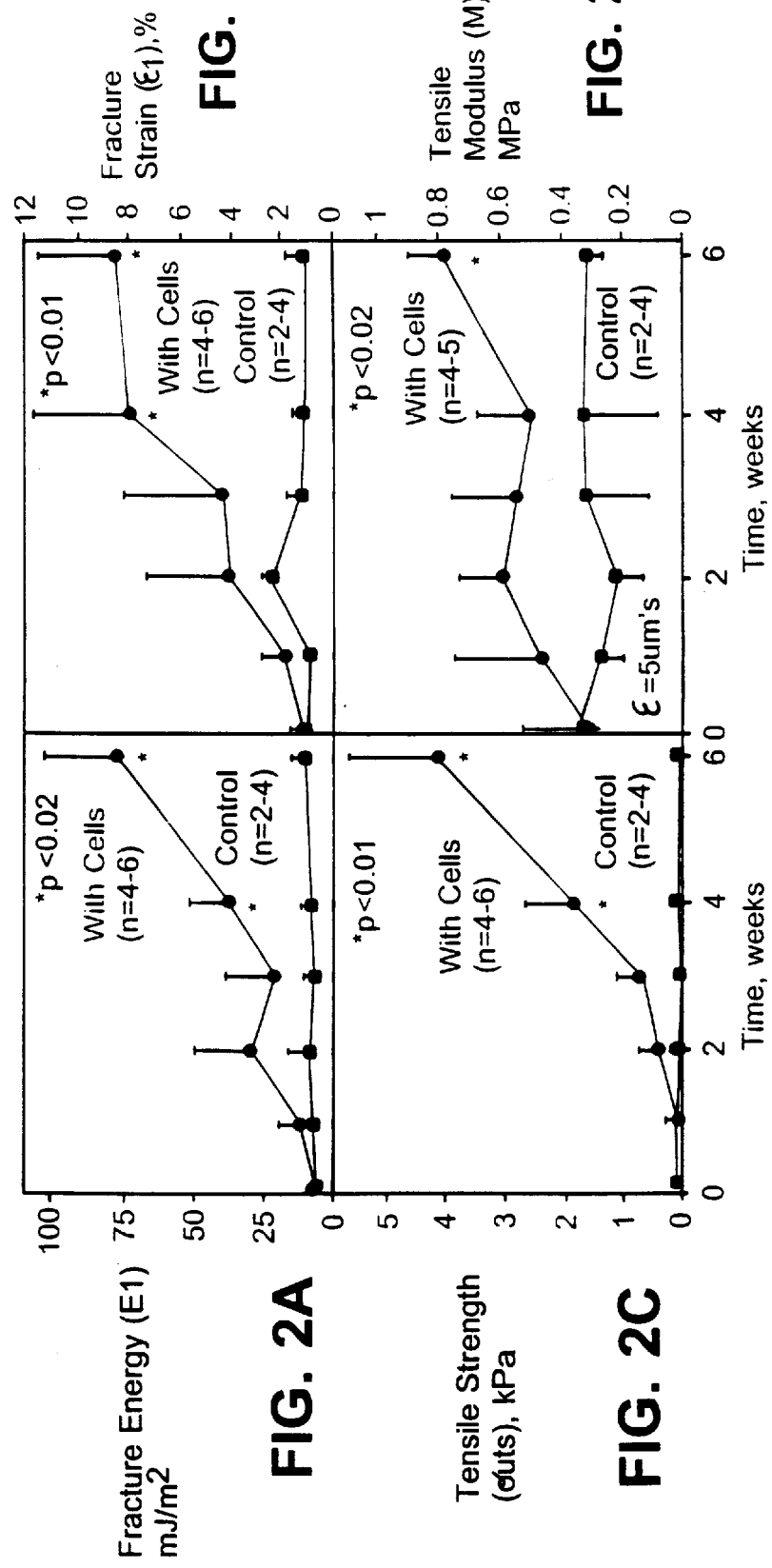

BONDING OF CARTILAGE PIECES USING ISOLATED CHONDROCYTES AND A BIOLOGICAL GEL

CROSS REFERENCE TO RELATED APPLICATIONS

This application claims priority from U.S. Provisional Application No. 60/064,451, filed Oct. 30, 1997.

STATEMENT AS TO FEDERALLY FUNDED RESEARCH

This invention was made with government support under National Institutes of Health Grant AR31068.

FIELD OF THE INVENTION

The field of the invention is cartilage repair.

BACKGROUND OF THE INVENTION

Cartilage, which is a heterogeneous tissue, can be classified as either articular or epiphyseal/physeal. Disturbances in cartilage structure and function are seen in congenital, infectious, traumatic, degenerative and neoplastic conditions. Biological repair of focal articular cartilage defects has generated great interest, yet some of the variables of this process have not been precisely defined (see, e.g., Brittberg et al., *New Engl. J. Med.*, 331:889–895, 1994; and Mankin, *New Engl. J. Med.*, 331:940–941, 1994). Such variables include the biochemical and biomechanical properties of the repair tissue itself and also its bonding with adjacent cartilage and bone.

The morphogenetic scaffold to which chondrocytes may attach and form matrix is one of the variables that have effects on the repair tissue. Materials that have been used as the scaffold include collagen gel (Fujisato et al., *Biomaterials*, 17:155–162, 1995; Hansen et al., *Clin. Orthop.*, 256:286–298, 1990; Mizuno et al., *Exp. Cell. Res.*, 227:89–97, 1996; Nixon et al., *Am. J. Vet. Res.*, 54:349–356, 1993; Sams et al., *Osteoarthr. Cartil.*, 3:47–59, 1995; Sams et al., *Osteoarthr. Cartil.*, 3:61–70, 1995), fibrin glue (Hendrickson et al., *J. Orthop. Res.*, 12:485–497, 1994; Homminga et al., *Acta Ortopedica Scandinavica*, 64:441–445, 1993; Tsai et al., *J. Formosan Med. Assoc.*, 3(Suppl):239–245, 1993), polyglycolic acid (Freed et al., *Biotechnology*, 12:689–693, 1994; Vacanti et al., *Am. J. Sports Med.*, 22:485–488, 1994), polyethylene oxide gel (Sims et al., *Plast. Reconstr. Surgery*, 98:843–850, 1996), alginate gel (Van Susante et al., *Acta Ortopedica Scandinavica*, 66:549–556, 1995), carbon fiber pads (Brittberg et al., *Clin. Orthop.*, 326:270–283, 1996) and xenogeneic matrix (Caruso et al., *J. Orthop. Res.*, 14:102–107, 1996).

Isolated and cultured chondrocytes embedded in these various scaffolds have been used for filling and repairing articular cartilage defects in chicks (Itay et al., *Clin. Orthop.*, 220:284–303, 1987), rabbits (Grande et al., *Anatomical Records*, 218:142–148, 1987; Grande et al., *J. Orthop. Res.* 7:208–218, 1989; Wakitani et al., *J. Bone Joint Surg. [Br.]*, 71:74–80, 1989), dogs (Shortkroff et al., *Biomaterials*, 17:147–154, 1996), and horses (Hendrickson et al., supra; Sams et al., *Osteoarthr. Cartil.*, 3:47–59, 1995; Sams et al., *Osteoarthr. Cartil.*, 3:61–70, 1995).

Complete repair of partial defects of cartilage implies side-to-side joining of cartilaginous matrices. While such joining has been investigated in several ways (Hunziker et al., *Trans. Orthop. Res. Soc.*, 17:231, 1992; Reindel et al., *J. Orthop. Res.*, 13:751–760, 1995; Wolohan et al., *J. Orthop. Res.*, 9:180–185, 1991), options for accomplishing this still need to be expanded.

SUMMARY OF THE INVENTION

The present invention is based on the discovery that isolated chondrocytes can propagate in the presence of an appropriate biological gel (e.g., fibrin gel) and generate cartilage matrix that firmly bonds two adjacent cartilage pieces.

Accordingly, the invention features a method of bonding two cartilage pieces. In this method, a bonding composition containing isolated chondrocytes mixed with a biological gel is applied to a surface of one (or both) of the cartilage pieces, and the surface is then contacted with the other cartilage piece. New cartilage matrix generated by the bonding composition will provide durable (e.g., 1% or more of normal cartilage strength) bonding between the two contacting cartilage pieces. The order of steps in the above-described method can be altered. For instance, the two cartilage pieces to be bonded can be held in apposition, and then the bonding composition is applied to fill gaps at the interface of the two cartilage pieces.

In another method of the present invention, either or both of the cartilage pieces are first incubated with isolated chondrocytes. A biological gel is then applied to a surface of either or both of the two pieces, and the two pieces are held together at the surface. Alternatively, the two cartilage pieces to be bonded can be held in apposition first to form a cartilage composite; after the composite is incubated with isolated chondrocytes, a biological gel is applied to fill gaps at the interface of the two cartilage pieces.

Isolated chondrocytes are chondrocytes that are separated from cartilage matrix, and they can be obtained from cartilage tissue or bone marrow. Both freshly isolated and cultured chondrocytes can be used.

A biological gel is a flexible, biodegradable (i.e., bioresorbable) and biocompatible (i.e., has no or negligible in vivo toxicity and is compatible with in vivo conditions) composition that typically has pores large enough to allow chondrocytes to populate. An exemplary biological gel is fibrin gel (also called fibrin glue). Fibrin gel has been used as the basis of many biological glues or adhesive matrices, and can be prepared with coagulation factors including thrombin and fibrinogen. Fibrinogen is cleaved by thrombin to form fibrin at the initiation of clotting.

One or both of the cartilage pieces to be bonded can be depleted of endogenous (i.e., innate) chondrocytes before the isolated chondrocytes are applied. The cartilage pieces to be bonded can be articular cartilage, fibrocartilage or growth cartilage, and can be obtained from the patient to be treated, or from a donor of the same or different species.

The new methods can be used to repair (i.e., resurface), in a mammal (e.g., human, mouse, rat, dog, horse, lamb, sheep, etc.), articular cartilage having a defect (e.g., a partial or full thickness defect); in that case, one of the two pieces to be bonded is the defective cartilage, and the other piece constitutes a part of a cartilage implant, and the chondrocytes used can be derived from the mammal itself. The present methods can also be used to treat defects in other types of cartilage, e.g., a meniscal tear in fibrocartilage or a resection defect resulting from excision of a physeal bar from an injured growth plate.

Also featured in the invention is a method of preparing a cartilage implant. In this method, a cartilage piece (e.g., one that contains no or essentially no viable endogenous chondrocytes) of appropriate size and shape is first co-cultured with isolated chondrocytes, and then a biological gel is applied to the cartilage piece to generate an implant. Alternatively, a bonding composition as described above can be applied directly the cartilage piece to generate an implant.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples described herein are illustrative only and not intended to be limiting.

Other features and advantages of the invention will be apparent from the following detailed description, and from the claims.

BRIEF DESCRIPTION OF THE DRAWINGS

FIGS. 1A and 1B are graphs showing applied tensile displacement and measured tensile load, respectively, from an experimental cartilage composite seeded with isolated chondrocytes and implanted in vivo for 21 days.

FIG. 1C is a graph showing a stress-strain curve generated from data shown in FIGS. 1A and 1B by normalizing displacement data to measured sample thickness and load data to sample area. $S_{UTS}$ stands for ultimate tensile strength, $\epsilon_f$ for fracture strain, M for dynamic tensile modulus, and $E_f$ for fracture energy.

FIGS. 2A–2D are graphs showing the time course of changes in tensile strength, fracture strain, fracture energy, and tensile modulus, respectively, of experimental and control cartilage composites. The composites were implanted in nude mice for the time period indicated on the horizontal axis. All data are shown as mean±SD, with the number of data points at each time point ranging from 4 to 6 for experimental composites and 2 to 4 for controls. In each of the four figures, "*" denotes appropriate p value for significance of difference between the experimental group and the control group at that time point.

DETAILED DESCRIPTION OF THE INVENTION

The methods of the invention are useful for bonding two or more cartilage pieces. In one of these methods, one first obtains a bonding composition comprising isolated chondrocytes mixed with a biological gel (e.g., about $10^5$ to $10^7$ cells/per ml gel), and then applies the bonding composition to the interface of the two cartilage pieces. Alternatively, one can first co-culture one or both of the cartilage pieces (e.g., devitalized pieces) with isolated chondrocytes (at a concentration of about $10^5$ to $10^7$ cells/per ml medium), and then apply a biological gel to the interface of the pieces. The chondrocytes that have infiltrated the cartilage pieces will then migrate into the gel.

The biological gel serves as a biodegradable and biocompatible scaffold on which the chondrocytes will proliferate and generate durable cartilage matrix. Biological gels that may be used include, but are not limited to, collagen gel, fibrin glue, polyglycolic acid, polylactic acid, polyethylene oxide gel, alginate or calcium alginate gel, poly-(2-hydroxyethyl methacrylate) (i.e., a hydrogel), polyorthoester, hyaluronic acid, polyanhydride, gelatin, agarose, and other bioresorbable and biocompatible materials such as those described in EP 0705878 A2. To promote chondrocyte proliferation and function, the biological gel can additionally contain appropriate nutrients (e.g., serum, salts such as calcium chloride, ascorbic acid, and amino acids) and growth factors (e.g., somatomedin, basic fibroblast growth factor, transforming growth factor β, cartilage growth factor, bone-derived growth factor, or a combination thereof). Selection of the optimal biological gel can be made using the guidance provided in the Examples below.

Chondrocytes useful in the new methods can be isolated from, e.g., articular cartilage or epiphysial growth-plate, by digestion with collagenase and optionally trypsin. Mesenchymal cells obtained from bone marrow can also be differentiated into chondrocytes under appropriate culture conditions as described by, e.g., Butnariu-Ephrat et al., *Clinical Orthopaedics and Related Research*, 330:234–243, 1996. Other sources from which chondrocytes can be derived include dermal cells and pluripotent stem cells.

The methods of the invention can be used to repair defective articular cartilage. To do so, a cartilage piece cut into the shape and size of a defect (see, e.g., Chu et al., *Arch. Am. Acad. Orthop. Surg.*, 1:9–14, 1997) is press-fitted and bonded to the defect. The cartilage implant can be, for example, autogeneic, isogeneic (e.g., from an identical twin), allogeneic, or xenogeneic. Before new cartilage matrix is generated at the interface of the implant and the host bed, resulting in a durable bonding between the implant and the host bed, the implant can be held in place by, e.g., bioresorbable pins (see, e.g., Chu et al., supra), or a piece of periosteal/perichondrial tissue sutured over the site of implantation (see, e.g., Minas et al., *Orthopedics*, 20:525–538, 1997; and WO 97/30662). One can also select an adhesive biological gel (e.g., fibrin gel) that provides temporary adhesion between the two cartilage pieces. The chondrocytes used for repairing cartilage defects can be, e.g., autogeneic, isogeneic, or allogeneic. Before implantation, the host cartilage to be repaired can be treated with, e.g., an enzyme, to remove proteoglycans and other substances that may interfere with the bonding.

The following examples are meant to illustrate the methods and materials of the present invention. Suitable modifications and adaptations of the variety of conditions and parameters normally encountered in bonding cartilaginous matrices which are obvious to those skilled in the art are within the spirit and scope of the present invention.

EXAMPLE I

Preparation of Cartilage Implant

Materials and Methods

Chondrocyte Isolation

Articular cartilage was harvested from lamb hips and shoulders by removing the superficial layers of articular cartilage under sterile conditions. The subchondral bone was avoided. Cartilage pieces were incubated for 8 hours at 37° C. in HAM's medium with Glutamax-1 (GibcoBRL, Grand Island, N.Y.) containing 0.075% collagenase Type 2 (Worthington Biochemical Co. Freehold, N.J.), 10% fetal bovine serum (Sigma, St. Louis, Mo.), 50 µg/ml ascorbic acid, 1% antibiotic/antimycotic solution (Sigma; each ml of the solution contains 10,000 units Penicillin, 10 mg Streptomycin, and 25 µg Amphotericin B in 0.9% NaCl), and L-glutamine 292 mg/l. Subsequent to the incubation, undigested tissue and debris were removed by filtering the cell suspension through a sterile nylon gauze.

Processing of Allogeneic Matrix

Slices of articular cartilage, each measuring approximately 3 millimeters ("mm") in width, 5 mm in length, and 1 mm in thickness, were harvested from knees and shoulders of unrelated lambs under sterile conditions. They were then placed in 50 ml test tubes containing phosphate buffered saline ("PBS") and 2% of the antibiotic/antimycotic solution (Sigma) and frozen at minus 20° C. for five days. After thawing, the PBS solution was discarded and the cartilage slices were subjected to five cycles of freezing and thawing in the absence of PBS.

Next, chondrocyte viability was evaluated in exemplary pieces by Trypan blue staining (Trypan blue 0.2%, Sigma) and fluorescence microscopy as previously described (Vacanti et al., supra). This procedure revealed that the cyclic freezing and thawing had killed all the innate chondrocytes in the cartilage slices. Cartilage slices with no detectable chondrocytes were termed "non-viable cartilage matrix" or "devitalized cartilage matrix."

Co-Culturing of Chondrocytes with Allogeneic Matrix

The cell suspension obtained as described above was centrifuged at 4000 rpm for ten minutes, and washed in PBS containing 2% of the antibiotic/antimycotic solution. Viability of chondrocytes was assessed by Trypan blue staining and recorded as a percentage of viable chondrocytes per high power field. Only those chondrocyte cultures having a viability score of 90% or greater were used in further studies described below. The exact cell count per ml was established using a hemocytometer. Chondrocyte solutions were adjusted to a concentration of $10^6$ cells/ml prior to use.

Co-culturing of chondrocytes with allogeneic matrix was performed by placing three slices of non-viable cartilage matrix in a 12 ml test tube (Corning, N.Y., USA) containing 4 ml of F12 medium (Sigma) and 1 ml of the adjusted chondrocyte solution. The cartilage slices and the chondrocytes were co-cultured in the F12 medium for 21 days. Control samples that contained no chondrocytes were kept under the same culture condition. In all cultures, the medium was changed twice weekly. For experimental groups, the fresh medium contained $10^6$ chondrocytes/ml.

Preparation of Matrix Composites

After co-culturing, the three cartilage slices infiltrated with chondrocytes (i.e., experimental slices) were removed from the media. This was done by placing the test tube on a vortex machine to re-suspend chondrocytes that were only loosely attached to the cartilage slices. The medium was then removed by aspiration, and the cartilage slices were re-suspended in fresh medium.

After this washing procedure was repeated several times, the three cartilage slices were placed onto a sterile Petri dish, and stacked on a sterile 27 gauge insulin needle by piercing each one through the center. Then, fibrin glue gel made from human cryoprecipitate and bovine thrombin (USP-Thrombostat, Parke Davis Lambert Co, Morris Plains, N.J.) was applied around the three slices to form a composite cartilage unit. The fibrin glue set in a few minutes, and the needle was subsequently removed.

Control composites were made with non-viable cartilage slices that had not been co-cultured with isolated chondrocytes.

Animal Model

Implantation of experimental and control matrix composites was performed under sterile conditions in a laminar flow hood. The composites were implanted into subcutaneous pouches at four sites in the backs of nude mice. Two experimental and two control composites were implanted in each animal. After sacrifice of the animals, cartilage composites were recovered under sterile conditions and evaluated as described below.

Evaluation of Composites Recovered from Mice

As shown in Table 1, three separate animal groups were employed for three different studies.

The first group, which consisted of 4 mice (each with four composites), was used to assess the bonding and histology of the matrix composites at various times (i.e., at 7, 14, 21, 28 and 42 days following implantation). The composites were examined with a pair of jeweler's forceps for the existence of fusion at the contact planes between the adjacent cartilage slices and separatability of the slices by the forceps' opening force. Each composite of three cartilage slices had two contact planes. The data on bonding between the cartilage slices presented below and in Table 2 refer to the 16 contact planes in the 8 experimental cartilage composites and to the 16 contact planes in the 8 control cartilage composites for each time period. A rank order scale was used to record the bonding between the cartilage slices. When the cartilage slices were completely fused with one another at their contact planes, a value of one was assigned. When any separation at all between slices was produced by the forceps, a value of zero was assigned. Bonding was expressed in absolute numbers and percentages per group. Composites used for histological analysis were fixed in 10% phosphate buffered formalin, embedded in paraffin, sectioned at five micrometers, stained with Safranin-O, and examined under a light microscope at 200× or 400×.

TABLE 1

| Study group | Time periods: | Day 0 (not implanted) | Day 7 | Day 14 | Day 21 | Day 28 | Day 42 | Totals |
|---|---|---|---|---|---|---|---|---|
| Number of implants for surfaces bonding evaluation and histologic analysis | Experimental | 8 | 8 [4] | 8 [4] | 8 [4] | 8 [4] | 8 [4] | 48 [20] |
| | Control | 8 | 8 | 8 | 8 | 8 | 8 | 48 |
| Number of implants for [$^3$H] Thymidine incorporation analysis | Experimental | 8 | — | 8 [4] | — | 8 [4] | 8 [4] | 32 [12] |
| | Control | 8 | — | 8 | — | 8 | 8 | 32 |
| Number of | Experimental | 8 | — | 8 | — | 8 | 8 | 32 |

TABLE 1-continued

| Study group | Time periods: | Day 0 (not implanted) | Day 7 | Day 14 | Day 21 | Day 28 | Day 42 | Totals |
|---|---|---|---|---|---|---|---|---|
| implants for fluorescence microscopy evaluation | Control | 8 | — | [4] 8 | — | [4] 8 | [4] 8 | [12] 32 |
| Totals: | Experimental | 24 | 8 [4] | 24 [12] | 8 [4] | 24 [12] | 24 [12] | 88 [44] |
|  | Control | 24 | 8 | 24 | 8 | 24 | 24 | 88 |

The number of nude mice used are recorded in brackets []. The composites were inserted into subcutaneous pouches on the back of the mouse at four different sites. Two experimental and two control composites were randomly assigned to and implanted in the two cranial and two caudal sites

TABLE 2

| DAY | Experimental group Bonding | Control group Bonding |
|---|---|---|
| 0 | 0/16 (0%) | 0/16 (0%) |
| 7 | 0/16 (0%) | 0/16 (0%) |
| 14 | 4/16 (25%) | 0/16 (0%) |
| 21 | 12/16 (75%) | 0/16 (0%) |
| 28 | 16/16 (100%) | 0/16 (0%) |
| 42 | 16/16 (100%) | 0/16 (0%) |

The second group, which consisted of 12 mice (each with four composites), was divided evenly into 3 subgroups for evaluating chondrocyte division at 14, 28, and 42 days, respectively, following implantation surgery. To evaluate chondrocyte division, each recovered composite was incubated with 16 $\mu$Ci/ml of [$^3$H] thymidine for 24 hours in an atmosphere of 92% air and 8% $CO_2$. Each composite was then hydrolyzed and combined with 3 ml of CYTOSCINT™ (ICN, Costa Mesa, Calif.). Radioactivity counts released from the composite were determined with a BECKMAN LS5000TD $\beta$-scintillation counter (Beckman, Fullerton, Calif.).

The third animal group consisted of 12 mice as well, and was used to evaluate composites recovered therefrom by fluorescence microscopy. Fifteen 100 $\mu$m thick sections of experimental and control cartilage composites were prepared using a 752M VIBROSLICE™ microtome (Campden Instruments LTD, Loughborough, England). These sections were then incubated with 100 $\mu$l of fluorescent dye solution (consisting of 3 $\mu$l calcein AM and 8 $\mu$l ethidium homodimer in 5 ml PBS; Molecular Probes, Eugene, Oreg.) for 1 hour. Cell viability within the matrix of experimental and control cartilage composite units was assessed on fresh 100 $\mu$m thick sections using a fluorescent microscope (Nikon MICROPHOT-FX™, Garden City, N.Y.). The calcein is taken up by viable cells and strongly fluoresces green, which is seen as a region of high light intensity on black and white photographs. The ethidium homodimer passively enters non-viable cells and weakly fluoresces red, which is seen as a region of low light intensity on black and white photographs.

Baseline values on composites prior to implantation were obtained for bonding (0/16), histology, [$^3$H] thymidine incorporation and fluorescence.

Statistical Analysis

Unpaired Student's t tests were used to compare [$^3$H] thymidine incorporation values (mean±SD) collected throughout the time periods examined. The Bonferroni modification was employed to maintain a type I error rate of 0.05 across all comparisons. In addition, experimental and control values during each session of the study were compared by means of unpaired Student's t tests ($p<0.05$).

Results

Starting at day 7 after implantation, fibrous capsules were formed by the fibrin glue previously applied to hold the pieces together, and they thickened with time. The capsules were removed for evaluation of bonding. The bonding of the experimental matrices infiltrated with viable chondrocytes increased with time until all such specimens were united at approximately days 28 to 42. Macroscopic view of the experimental composites at 42 days following implantation revealed that, while the original slices of matrix were discernible, the composite had united into a solid cartilaginous mass. However, at all time points examined, the cartilage pieces in the control composites slid apart spontaneously and immediately after the removal of the fibrous capsule. Thus, the distinction between success and failure in bonding was easy to discern.

Histological evaluation showed that, prior to implantation, the experimental composites had live chondrocytes on the surface of their devitalized cartilage slices, whereas only some nuclear debris of dead cells but no vital cells were found in control composites.

Microscopic examination of cartilage composites recovered after implantation revealed that chondrocytes were forming matrix at the contact planes between the allogeneic slices of experimental composites, and that this new cartilage layer increased in thickness from day 7 to day 42. At day 7 after implantation, viable chondrocytes forming matrix were seen on the contacting surfaces of cartilage slices, and the fibrin glue formed a relatively thick layer between the contact surfaces. At day 14, each layer of viable chondrocytes had increased in thickness, and the fibrin glue layer had shrunk. By day 21, the contact space between the elliptically shaped allogeneic matrices was filled with viable chondrocytes making new matrix, and the fibrin glue had been mostly absorbed. 28 days following implantation, the entire contacting region between adjacent cartilage slices was filled with new cartilage. Buds of new cartilage started to grow into the devitalized matrices. At day 42, more ingrowth of the buds, some of which had branches, was seen, and loss of Safranin-O staining of the devitalized matrix occurred around the new cartilage, indicating that matrix-generating chondrocytes were invading the devitalized matrix. By this time, new cartilage, the organization of which grossly resembled that of mature cartilage, had entirely filled the holes in the cartilage slices created by the needle used during composite assembly with fibrin glue. Safranin-O staining in the new cartilage had also increased. Several mitotic figures were encountered in the new cartilage layer at every time period.

The control composites, on the other hand, showed no new matrix formation at any time point examined. Sectioning of these composites could be accomplished only because of the surrounding fibrous capsule. The capsule stained only with the Fast Green counter-stain and not Safranin-O. No viable chondrocytes were found present.

Examination of chondrocyte division showed a statistically significant decrease in [$^3$H] thymidine incorporation into the experimental composites from day 0 (about 85,000 counts per minute or cpm) to day 28 (about 10,000 cpm), followed by an increase at day 42 (about 43,000 cpm). The differences at the various time points for the experimental composites were significant, with p less than 0.01 in Student' t test. Incorporation of [$^3$H] thymidine into control composites was not significantly different from baseline (about 2,000 cpm) at any time period. The differences between the experimental and control groups were significant ($p<0.05$) at each time point examined (i.e., days 0, 14, 28, and 42).

Examination of the experimental composites with fluorescence microscopy (at 100x) confirmed that the growth of the new matrix was occurring with a concomitant increase in viable chondrocytes interstitially. Fluorescence staining of experimental composites at day 42 revealed that the devitalized matrices did not take up calcein, whereas the new cartilage layer formed between neighboring matrices fluoresced brightly with calcein, indicating the presence of viable cells in the layer. Buds of new cartilage that fluoresced brightly with calcein were also seen penetrating the devitalized matrix. Viable clusters of chondrocytes were seen within the allogeneic matrices at days 28 and 42.

EXAMPLE II

Biomechanical Assessment of Cartilage Bonding

To test the strength of the bonding formed between two cartilage disks as described in the above Example, the pair of bonded disks were glued onto plexiglass rods and mounted in the jaws of a testing machine. The bonded slices were pulled to failure in tension as indicated by either visible separation of cartilage disks or when the measured load was observed to be less than 0.05 Newton. Resultant loads were recorded on a personal computer, and data were collected at a rate of 5 points/second. Sample pairs were kept hydrated with PBS throughout testing.

Applied displacements and measured loads were normalized to sample thickness and area, and using these data, a stress-strain curve was constructed for each sample. From the stress-strain curve, the ultimate tensile strength ($S_{UTS}$) was determined by inspection as the strain at which further increases in strain produced lower stresses. The fracture strain ($\epsilon_f$) was also determined by inspection. The fracture energy ($E_f$), defined as the area under the stress-strain curve until failure, was calculated numerically using a Reimann sum method with the partition element given by the strain interval between data points. The dynamic tensile modulus (M) for the given strain rate of each sample was calculated as the slope of the linear portion of the stress-strain curve using a standard least squares algorithm.

Cartilage composites implanted in nude mice as described in Example I were retrieved at a weekly interval for up to 6 weeks. Tensile strength, fracture strain, fracture energy, and tensile modulus of the cartilage bonding formed in these composites were assessed. The values of these parameters are indicative of bonding strength. Data shown in FIGS. 2A–2D demonstrated that the values of the four parameters were significantly higher in cartilage composites containing isolated chondrocytes than in composites not containing chondrocytes. The values also increased steadily with time in the former composites, and by week 6, reached 5–10% of the corresponding values of normal articular cartilage.

After biomechanical tests, samples were retrieved for histological evaluation. Histological evaluation was also performed on a few samples that were not biomechanically tested. For pre- and post-test histological analysis, specimens were fixed in 10% phosphate buffered formalin and embedded in paraffin. Serial sections that were 5 $\mu$M thick were obtained and stained with Safranin-O.

Histological analysis of biomechanically tested samples indicated that failure of bonding occurred at the interface between the new and devitalized cartilage in experimental groups or between the two discs of cartilage for controls. After the two layer of new matrix fused at about day 21, failure was never observed in the thickness of the new tissue, but always at the interface of the newly formed matrix and the devitalized cartilage.

In samples fixed during testing, newly formed tissue was pulled away from devitalized cartilage matrix. This was analogous to an apparent crack propagating along the interface between new and devitalized matrix. Observation of this process revealed that, in vicinity of the crack tip, cells along the fracture line appeared to be elongated in the direction perpendicular to the line of crack propagation. Occasionally, fractures occurred in opposite sides and both propagated towards the center, leaving an intact connection.

In case where chondrocytes penetrated devitalized matrix, fracture occurred at the opposing interface in 80% of the sections sampled.

As shown above, the strength of the interface between the new tissue and existing matrix increases with time, demonstrating remodelling of the new tissue, even after the space between the pieces of matrix has been filled with new tissue. Although the total fusion of the two layers of new matrix occurred at about day 21, as shown by the histology, the biomechanical study showed an increase of the strength of the repair tissue at further evaluation times (days 28 and 42). This phenomenon could be explained by the formation of buds of penetration from the new tissue into the devitalized matrix, stabilizing the construct and making the interface stronger; this is consistent with histological finding that in 80% of sections sampled, failure occurred on the opposite interface when penetration were present.

EXAMPLE III

Meniscus Repair

This example applies the cartilage repair procedure of Example I to meniscus repair.

Articular cartilage was harvested from lamb joints, and the chondrocytes isolated as described in Example I above. Meniscus chips were harvested from the knees of lambs of the same species.

Menisci were harvested from unrelated lambs, and each meniscus was divided into three parts. The vascularized portion was removed from the avascular zone of each part, and the menisci were devitalized using five freeze/thaw cycles. A 4 mm-long buckle handle lesion (also called a fracture) was carved into each meniscus about 2 mm from the free margin of the avascular zone.

The devitalized chips were co-cultured with lamb chondrocytes as described in Example I. The menisci were divided into four groups. In group A, a chip seeded with chondrocytes was sutured inside the buckle handle fracture of the meniscus. In group B, an unseeded chip was sutured onto the fracture. In group C, the meniscus fracture was sutured without a chip. In group D, the fracture was left untreated (no suturing).

The fibrin glue gel described in Example I was then applied to the meniscus samples in each group so as to surround the samples with the gel. Each of two samples from each group was implanted into the subcutaneous pouch of a nude mouse, totalling eight mice in all.

After 14 weeks, the meniscus samples were removed from the mice, grossly and histologically examined, and tested for cartilage repair as described in Example I. The samples from group A kept their shape and were fully repaired, while the samples from groups B–D did not indicate any repair.

EXAMPLE IV

Clinical Repair of Articular Cartilage

This example describes a prophetic protocol (adapted from Chu et al., supra) for repairing a full thickness articular cartilage defect in a knee joint of a human.

The surgical procedure entails entry of the knee joint through a standard midline incision. The damaged articular surface is removed with an osteotome in a rectangular pattern. Approximately 5 mm of subchondral bone is removed with a high-speed burr. The host bed is then measured.

A similarly sized and located allograft is removed from a fresh cadaver knee of a healthy donor. The cadaver knee matches the defective knee in size, as determined by the anteroposterior dimension of the tibial plateau on standard radiographs. The allograft subchondral bone is tailored with a burr to a thickness of 5 to 10 mm. Pulsatile lavage is used to flush out cellular elements from the marrow. A bonding composition containing fibrin gel and chondrocytes derived from the bone marrow of the patient (about $10^6$ cells/ml) is applied to the host bed and the allograft at places where the two will contact. The allograft is then press-fitted into the host bed and positioned about 1 to 2 mm above the articular surface of the host bone. Resorbable pins are used for temporary internal fixation.

OTHER EMBODIMENTS

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A method for side-to-side bonding of a first fibrocartilage matrix to a second fibrocartilage matrix comprising:

providing a bonding composition comprising isolated chondrocytes mixed with a biological gel that serves as a scaffold for the chondrocytes;

holding the first fibrocartilage matrix together with the second fibrocartilage matrix so that a side of the first fibrocartilage matrix is in apposition to a side of the second fibrocartilage matrix and gaps remain at the interface between the two sides; and filling the gaps at the interface between the two sides with the bonding composition to bond the first fibrocartilage matrix to the second fibrocartilage matrix.

2. The method of claim 1, wherein the side of the first fibrocartilage matrix is one side of a meniscal tear, and the side of the second fibrocartilage matrix is the opposite side of a meniscal tear.

3. The method of claim 1, wherein the gel is formed from a material selected from the group consisting of: fibrin, collagen, polygycolic acid, polylactic acid, polyethylene oxide, alginate, calcium alginate, poly-(2-hydroxyethyl methacrylate), polyorthoester, hyaluronic acid, gelatin and agarose.

4. The method of claim 3, wherein the gel is a fibrin gel.

* * * * *